US006333507B1

(12) United States Patent
Lai et al.

(10) Patent No.: US 6,333,507 B1
(45) Date of Patent: Dec. 25, 2001

(54) SYSTEM FOR MEASURING CONCENTRATION OF CHEMICAL COMPOSITION OF FLUID

(75) Inventors: Lih-Huey Lai, Taipei; Hui-Rong Hsieh, Tainan, both of (TW)

(73) Assignee: Industrial Technology Institute, Hsinchu (TW)

( * ) Notice: Subject to any disclaimer, the term of this patent is extended or adjusted under 35 U.S.C. 154(b) by 0 days.

(21) Appl. No.: 09/482,577

(22) Filed: Jan. 13, 2000

(51) Int. Cl.[7] .......... G01J 1/58
(52) U.S. Cl. .......... 250/483.1; 250/458.1
(58) Field of Search .......... 250/458.1, 483.1, 250/484.2, 486, 461.2, 573, 576; 365/39, 40

(56) References Cited

U.S. PATENT DOCUMENTS 5,457,313 * 10/1995 Baylor et al. .......... 250/483.1
5,738,997 4/1998 Hayashi et al. .
5,973,330 10/1999 Hayashi .

* cited by examiner

*Primary Examiner*—Hung Xuan Dang
(74) *Attorney, Agent, or Firm*—Browdy and Neimark

(57) ABSTRACT

A system is designed to measure the concentration of a specific chemical composition of a fluid and is formed of a light generating device, a fluorescent light receiver, and a display. The light generating device emits an excitation light to cause a probe submerged in the fluid to emit fluorescent light, which is received by a photoelectric diode of the fluorescent light receiver and is than converted by the photoelectric diode into an electric current signal. The display receives the electric current signal, which is then converted by the display into the concentration of the specific chemical composition of the fluid. The information on the concentration of the specific chemical composition is exhibited on the display.

15 Claims, 1 Drawing Sheet

18
12
10
20
22
14
26
16
24

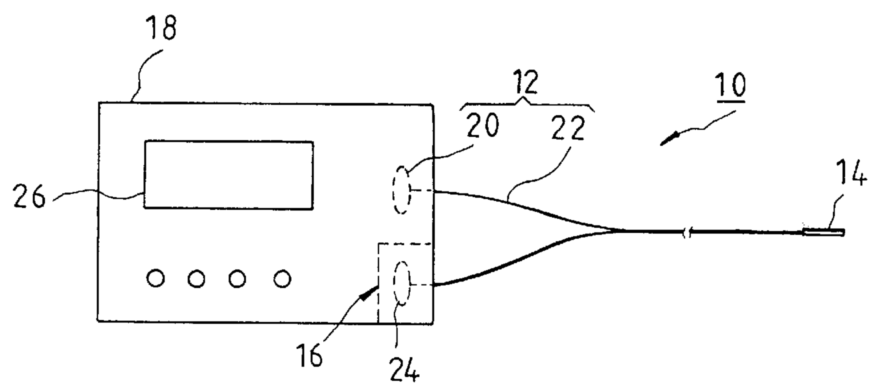
F I G. 1
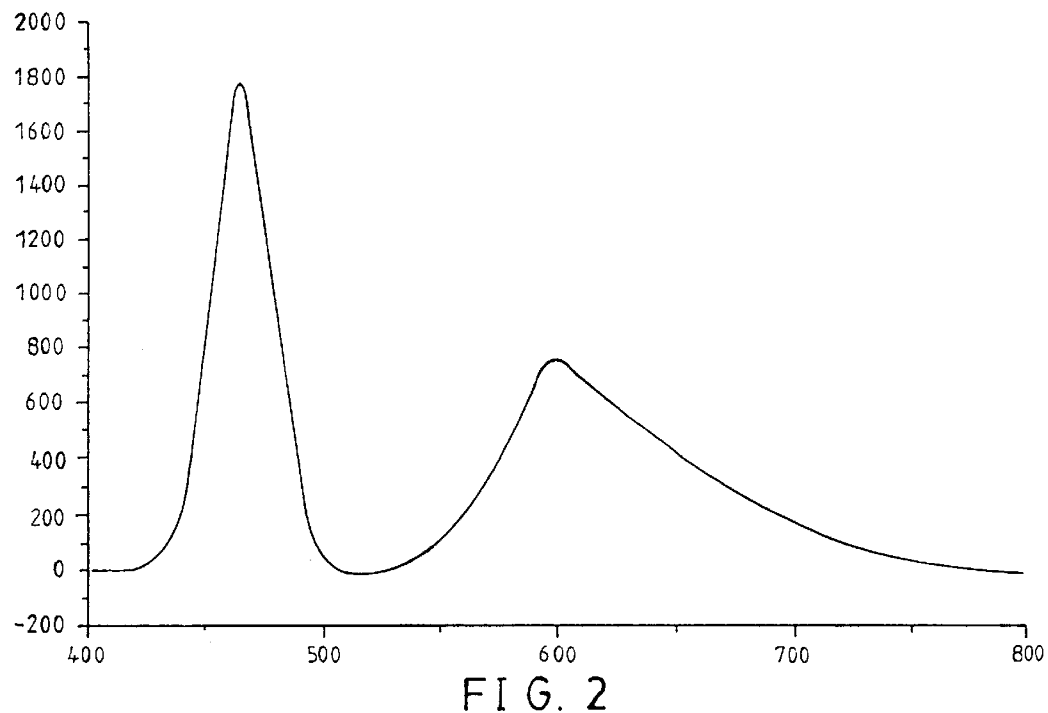
F I G. 2
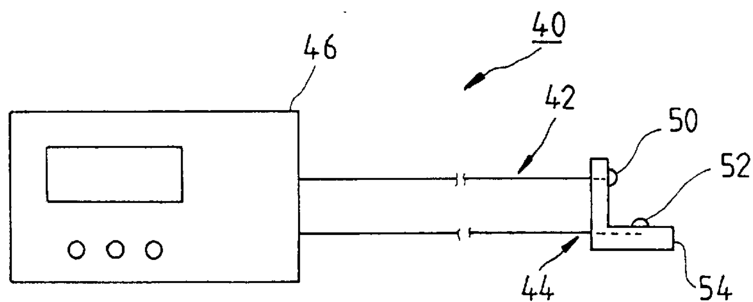
F I G.3

SYSTEM FOR MEASURING CONCENTRATION OF CHEMICAL COMPOSITION OF FLUID

FIELD OF THE INVENTION

The present invention relates generally to a system for measuring the concentration of a specific chemical composition of a fluid, and more particularly to a system involving the application of an excitation light source and a probe for measuring the concentration of the specific chemical composition of the fluid.

BACKGROUND OF THE INVENTION

According to the conventional practice, the concentration of a specific chemical composition, such as oxygen in a liquid or sulfur dioxide in a gas, is measured by the intensity of the fluorescent light emitted by the specific chemical composition. A probe kept in the fluid is irradiated by an excitation light source of a specific wavelength to emit fluorescent light of an intensity. The intensity of fluorescent light emitted by the probe is reduced at the time when the probe comes in contact with the specific chemical composition. This is due to the fact that the energy of the excited molecules on the probe is transmitted in a non-radiating manner to the molecules of the specific chemical composition. The energy is dissipated in the form of heat. The extent of reduction in intensity of the fluorescent light emitted by the probe is dependent on the concentration of the specific chemical composition such that the fluorescent light intensity is inversely proportional to the concentration of the specific chemical composition. As a result, the concentration of the specific chemical composition of the fluid can be calculated on the basis of the fluorescent light intensity of the probe. An alternative method makes no use of the probe. The fluid is irradiated by the excitation light source of a specific wavelength, thereby resulting in the fluorescent light emitted by the specific chemical composition. The intensity of the fluorescent light emitted by the specific chemical composition in a state of excitation is directly proportional to the concentration of the specific chemical composition. As a result, the concentration of a specific chemical composition can be calculated on the basis of the intensity of the fluorescent light emitted by the specific chemical composition.

Both methods described above have one thing in common that they make use of a grating or prism beam split to differentiate the excitation light and the fluorescent light. The spectral analysis of the fluorescent light is done by a spectrograph. The intensity of the fluorescent light is obtained on the basis of the data of the spectral analysis in conjunction with the integration circuit or the integration program. The concentration of the specific chemical composition is then compared and computed by the conversion equation. The concentration data are exhibited in a display.

Such conventional systems described above are capable of measuring the concentration of a specific chemical composition with precision; nevertheless they are not cost-effective in view of the complexity of the systems and the high cost of the spectrograph. The U.S. Pat. Nos. 5,973,330 and 5,738,997 disclose the similar technological applications in which the photosensor is used to receive the signal of fluorescent light. In addition, these two disclosures are also not cost-effective in view of the fact that they make use of the optical lenses, such as beam splitter, reflector, etc. to differentiate the excitation light and the fluorescent light which is brought about by the excitation light.

SUMMARY OF THE INVENTION

It is therefore the primary objective of the present invention to provide a simple and cost-effective system for measuring the concentration of a specific chemical composition of a fluid.

It is another objective of the present invention to provide a modular and compact system for measuring the concentration of a specific chemical composition of a fluid.

It is another objective of the present invention to provide a relatively simple device for measuring the intensity of the fluorescent light so as to streamline the conventional systems for measuring the concentration of a specific chemical composition of a fluid.

The system of the present invention comprises a light source generating device, a probe, a fluorescent light receiving device, and a display. The probe is submerged in a fluid and is irradiated by the excitation light generated by the light source generating device, so as to give off the fluorescent light, which is then converted into an electric current signal by a photoelectric diode of the fluorescent light receiving device. The electric current signal is received by the display in which the current signal is converted into the concentration of a specific chemical composition of the fluid. The concentration data are exhibited by the display. The system of the present invention may be carried out without the probe. Under such a circumstance, the fluid is irradiated by the excitation light such that a specific chemical composition is excited to emit the fluorescent light, which is then converted into an electric current signal. The concentration of the specific chemical composition is obtained by the display on the basis of the electric current signal.

BRIEF DESCRIPTION OF THE DRAWINGS

FIG. 1 shows a schematic view of the layout of a system of a first preferred embodiment of the present invention.

FIG. 2 shows a diagram of spectrum analysis of the excitation light and the fluorescent light of the first preferred embodiment of the present invention for measuring the concentration of oxygen contained in a fluid.

FIG. 3 shows a schematic view of the layout of a system of a second preferred embodiment of the present invention.

DETAILED DESCRIPTION OF THE INVENTION

As shown in FIGS. 1 and 2, a system 10 of the first preferred embodiment of the present invention is exemplified to measure the concentration of oxygen contained in a fluid. The system 10 comprises a light generating device 12, a probe 14, a fluorescent light receiver 16, and a display 18.

The light generating device 12 has a blue light-emitting diode (LED) capable of generating a narrow frequency excitation light of a wavelength of about 460 nanometer, as shown in FIG. 2. The probe 14 is irradiated by the excitation light under the guidance of an optical fiber 22. The excitation light may be also provided by laser, deuterium lamp, xenon lamp, etc. in place of the light-emitting diode.

The probe 14 is covered with a ruthenium complex and is capable of emitting the fluorescent light of a wavelength of 600 nanometer upon being irradiated by an excitation light of a wavelength of 460 nanometer, as shown in FIG. 2. The fluorescent light is then guided by an optical fiber 22 to the fluorescent light receiver 16. When the ruthenium complex comes in contact with oxygen of the solution, the energy of the excitation light is partially transmitted in a non-radiating manner to the oxygen molecule such that the energy is converted into heat, which is then dissipated. As a result, the intensity of the fluorescent light emitted by the probe 14 is reduced. The extent of reduction in intensity of the fluorescent light is related to the concentration of the oxygen molecule of the solution.

The fluorescent light receiver 16 comprises a photoelectric diode 24 responsive to the light of a specific range in wavelength. For example, the diode 24 of the first preferred embodiment of the present invention is responsive to the light having a wavelength greater than 500 nanometer. In other words, the diode 24 is responsive to the excitation light having a wavelength greater than 40 nanometer, so as to ensure that the light received by the diode 24 is the fluorescent light emitted by the probe 14. The fluorescent light is converted into an electric current signal. In the practical application of the fluorescent light receiver 16, a band-pass filler (not shown in the drawings) or a cut-off filter (not shown in the drawings) is disposed in front of the photoelectric diode 24 for preventing the photoelectric diode from being interfered by the excitation light source, so as to ensure that the photoelectric diode receives the fluorescent light of a specific wavelength.

The display 18 has a display screen 26, an integraph and a calculation circuit (not shown in the drawings). The integraph of the first preferred embodiment of the present invention is a capacitor (not shown in the drawings) which is electrically connected with the photoelectric diode 24 to achieve the function of accumulating the electric current signal, which is converted into the oxygen concentration by the calculation circuit. The oxygen concentration information is exhibited on the display screen 26.

The light source generating device 12, the probe 14, the display 18, and the calculation equation for converting the current signal of the intensity of fluorescent light into the concentration of the chemical composition are similar to the prior art devices. The present invention is characterized by the photoelectric diode which is responsive to only the fluorescent light of a specific range in wavelength. The photoelectric diode is readily available in the market place at a low price and is miniaturized to make the system as compact as possible. In addition, the photoelectric diode may be used in conjunction with a filter to measure the intensity of the fluorescent light.

As shown in FIG. 3, a system 40 of the second preferred embodiment of the present invention comprises a light generating device 42, a fluorescent light receiver 44, and a display 46. The system 40 is similar in construction to the system 10 described above, with the difference being that the former comprises a light-emitting diode 50 for use in generating an excitation light source, and a photoelectric diode 52 for use in receiving the fluorescent light. The diodes 50 and 52 are fixed in a probing seat 54, which is submerged in a fluid to be measured. The fluid is directly irradiated by the excitation light such that a specific chemical composition of the fluid is excited to emit the fluorescent light, which is received by the photoelectric diode 52 and is then converted into an electric current signal. The concentration of the specific chemical composition is computed by the display 46 on the basis of the electrical current signal. The concentration data are exhibited on the display 46.

The embodiments of the present invention described above are to be regarded in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. A system for measuring the concentration of a specific chemical composition of a fluid, said system comprising:

a light generating device for emitting an excitation light to cause a probe kept in the fluid to emit fluorescent light;

a fluorescent light receiver having a photoelectric diode for receiving the fluorescent light emitted by the probe and for converting the fluorescent light into an electric current signal; and a display electrically connected with said photoelectric diode for receiving the electric current signal and for converting the electric current signal into the concentration of the specific chemical composition whereby the concentration of the specific chemical composition is exhibited by said display.

2. The system as defined in claim 1, wherein said light generating device comprises an optical fiber for guiding the excitation light to the probe and for guiding the fluorescent light emitted by the probe to said photoelectric diode.

3. The system as defined in claim 1, wherein said photoelectric diode is responsive to the fluorescent light of a wavelength in a specific range whereby said specific range is greater than a wavelength of 40 nanometer of the excitation light.

4. The system as defined in claim 1, wherein said fluorescent light receiver further comprises a filter to enable said photoelectric diode to receive light of a wavelength of a specific range without said fluorescent light receiver being interfered by said excitation light.

5. The system as defined in claim 4, wherein said filter is a band-pass filter.

6. The system as defined in claim 4, wherein said filter is a cut-off filter.

7. The system as defined in claim 1, wherein said display has an integraph for accumulating the electric current signal.

8. The system as defined in claim 7, wherein said integraph is a capacitor.

9. A system for measuring the concentration of a specific chemical composition of a fluid, said system comprising:

a light generating device for emitting an excitation light to irradiate the fluid such that the specific chemical composition is excited to emit fluorescent light;

a fluorescent light receiver having a photoelectric diode for receiving the fluorescent light emitted by the specific chemical composition of the fluid whereby the fluorescent light received by said photoelectric diode is converted by said photoelectric diode into an electric current signal; and a display electrically connected with said photoelectric diode for receiving the electric current signal and for converting the electric current signal into the concentration of the specific chemical composition whereby the concentration of the specific chemical composition is exhibited by said display.

10. The system as defined in claim 9, wherein said photoelectric diode is responsive to the fluorescent light of a wavelength in a specific range whereby said specific range is greater than a wavelength of 40 nanometer of the excitation light.

11. The system as defined in claim 9, wherein said fluorescent light receiver further comprises a filter to enable said photoelectric diode to receive light of a wavelength of a specific range without said fluorescent light receiver being interfered by said excitation light.

12. The system as defined in claim 1, wherein said filter is a band-pass filter.

13. The system as defined in claim 1, wherein said filter is a cut-off filter.

14. The system as defined in claim 9, wherein said display has an integraph for accumulating the electric current signal.

15. The system as defined in claim 9, wherein said excitation light is emitted by a light-emitting diode; and wherein said photoelectric diode and said light-emitting diode are fixed on a probing seat whereby said probing seat is submerged in the fluid.

* * * * *

UNITED STATES PATENT AND TRADEMARK OFFICE

CERTIFICATE OF CORRECTION

PATENT NO. : 6,333,507 B1 Page 1 of 1
DATED : December 25, 2001
INVENTOR(S) : Lih-Huey Lai and Hui-Rong Hsieh It is certified that error appears in the above-identified patent and that said Letters Patent is hereby corrected as shown below:

Title page,
Item [73], Assignee, please change "Industrial Technology Institute" to -- Industrial Technology Research Institute --.

Signed and Sealed this

Twenty-fifth Day of October, 2005

JON W. DUDAS
*Director of the United States Patent and Trademark Office*